(12) United States Patent
Matsuda et al.

(10) Patent No.: US 10,054,529 B2
(45) Date of Patent: *Aug. 21, 2018

(54) PARTICLE COUNTER

(71) Applicant: RION Co., Ltd., Tokyo (JP)

(72) Inventors: Tomonobu Matsuda, Tokyo (JP); Masaki Shimmura, Tokyo (JP); Yuki Yamakawa, Tokyo (JP)

(73) Assignee: RION Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/555,376

(22) PCT Filed: Mar. 4, 2016

(86) PCT No.: PCT/JP2016/056787
§ 371 (c)(1),
(2) Date: Sep. 1, 2017

(87) PCT Pub. No.: WO2016/143696
PCT Pub. Date: Sep. 15, 2016

(65) Prior Publication Data
US 2018/0038781 A1  Feb. 8, 2018

(30) Foreign Application Priority Data

Mar. 6, 2015  (JP) ................. 2015-045175

(51) Int. Cl.
*G01N 21/00* (2006.01)
*G01N 15/02* (2006.01)
(Continued)

(52) U.S. Cl.
CPC ......... *G01N 15/0205* (2013.01); *G01N 15/06* (2013.01); *G01N 15/1434* (2013.01);
(Continued)

(58) Field of Classification Search
CPC ............ G01B 9/02024; G01B 9/02038; G01N 15/0211; G01N 15/06; G01N 15/1434;
(Continued)

(56) References Cited

U.S. PATENT DOCUMENTS 4,828,388 A   5/1989 Namba
5,061,070 A  10/1991 Williams
(Continued)

FOREIGN PATENT DOCUMENTS

JP  62291547  12/1987
JP  01245132   9/1989
(Continued)

OTHER PUBLICATIONS

Japanese Office Action dated Jul. 9, 2015 for the corresponding Japanese Patent Application No. 2015-045175 and its English translation.
(Continued)

*Primary Examiner* — Sunghee Y Gray
(74) *Attorney, Agent, or Firm* — Rankin, Hill & Clark LLP

(57) ABSTRACT

An irradiation optical system 12 irradiates a fluid flowing in a flow passage 2a with one light among a plurality of lights obtained by branching light from a light source 1 and forms the detection area. A detection optical system 13 makes scattered light with a different direction from an optical axis of the irradiation optical system enter a beam splitter 17 among the scattered lights from particles contained in the fluid in this detection area. Meanwhile, a beam expander 16 makes another light among the plurality of lights enter the beam splitter 17 as reference light. A detector 4 receives an interference light, by the scattered light and the reference light, obtained by the beam splitter 17 by light receiving elements and generates a detection signal corresponding to
(Continued)

the interference light. A counting unit 6 counts the particles based on this detection signal.

16 Claims, 5 Drawing Sheets

(51) Int. Cl.
  *G01N 15/06* (2006.01)
  *G01N 15/14* (2006.01)
  *G01N 21/45* (2006.01)
  *G01N 15/00* (2006.01)

(52) U.S. Cl.
  CPC ..... *G01N 21/45* (2013.01); *G01N 2015/0011* (2013.01); *G01N 2015/1445* (2013.01); *G01N 2015/1486* (2013.01)

(58) Field of Classification Search
  CPC ....... G01N 15/1459; G01N 2015/0687; G01N 2015/0693; G01N 2015/1454; G01N 2015/1486; G01N 15/0205; G01N 21/45; G01N 2015/0011; G01N 2015/1445
  USPC ........................................................ 356/337
  See application file for complete search history.

(56) References Cited

U.S. PATENT DOCUMENTS

| 2002/0101593 | A1 | 8/2002 | Yang et al. |
| 2009/0153857 | A1 | 6/2009 | Matsuda |
| 2011/0001969 | A1 | 1/2011 | Nakamura |
| 2014/0125992 | A1 | 5/2014 | Ota |
| 2014/0152986 | A1* | 6/2014 | Trainer .............. G01N 15/0205 356/336 |

FOREIGN PATENT DOCUMENTS

| JP | 01292235 | 11/1989 |
| JP | 04058137 | 2/1992 |
| JP | 06213795 | 8/1994 |
| JP | 06331529 | 12/1994 |
| JP | 11118699 A2 | 4/1999 |
| JP | 2001264232 A2 | 9/2001 |
| JP | 2007071794 A2 | 3/2007 |
| JP | 2007333409 A2 | 12/2007 |
| JP | 2009030988 A2 | 2/2009 |
| JP | 2011013162 A1 | 1/2011 |
| JP | 5134177 B2 | 11/2012 |
| JP | 5438198 B1 | 3/2014 |
| JP | 2014044095 A2 | 3/2014 |
| JP | 2014092425 A2 | 5/2014 |
| JP | 2014092525 A2 | 5/2014 |
| JP | 5859154 B1 | 2/2016 |

OTHER PUBLICATIONS

International Search Report dated May 17, 2016 filed in PCT/JP2016/056787.
Notice of Allowance dated Nov. 28, 2017 for the corresponding Korean Patent Application No. 10-2017-7026530.

* cited by examiner

PARTICLE COUNTER

TECHNICAL FIELD

This invention relates to a particle counter.

BACKGROUND ART

There have been provided particle counters as devices for measuring particles in fluids, which are, for example, liquids such as a chemical solution and water, or gas such as air. At the particle counter, a fluid containing particles is irradiated with a laser beam. Scattered light from the particles in the fluid is observed to count the particles (for example, refer to Patent Literature 1).

For example, in the manufacture of semiconductor wafers, the particles of impure substances contained in the chemical solution to be used exert influence on the manufacturing process. Accordingly, a particle counter is used to count the particles in the chemical solution to control the state of the chemical solution. In the chemical solution, scattered light (background light) and the like are generated by the medium (namely, the chemical solution itself). Thus, measuring particles in the chemical solution involves larger background noise than that in the case of measuring the particles in the water. This makes it difficult to count small-size particles (for example, 30 nm or less).

One particle counter uses a multi-divided light receiving element. The multi-divided light receiving element reduces the effective light receiving areas at end portions. As a result, reducing the noise resulting from the background light improves the signal-to-noise (S/N) ratio (for example, refer to Patent Literature 1).

Meanwhile, there has been proposed a dynamic light-scattering measuring device having a Mach-Zehnder interferometer and a low-coherence light source (for example, refer to Patent Literature 2). Such a dynamic light-scattering measuring device obtains a particle size distribution based on changes in scattered light intensity resulting from the Brownian motion of the particles.

CITATION LIST

Patent Literature

Patent Literature 1: Japanese Patent No. 5438198
Patent Literature 2: JP-A-2011-13162

SUMMARY OF INVENTION

Problems to be Solved by the Invention

The foregoing dynamic light-scattering measuring device can obtain a particle size distribution. However, since using the Brownian motion of particles, this device is not suitable for the counting of the particles in the fluid.

The foregoing particle counter can count the particles with the small particle size small to some extent. However, the counting of the particles with the smaller particle size has been requested. For example, there has been requested a particle counter that counts the particles with the particle size of 30 nm or smaller in the chemical solution in response to recent miniaturization of a process rule for manufacture of semiconductor wafers.

This invention has been made in consideration of the foregoing problem. An object of this invention to obtain a particle counter that can count particles with a small particle size in a fluid at a satisfactory S/N ratio.

Solutions to the Problems

A particle counter according to the present invention includes a light source, a light superimposition unit, an irradiation optical system, a detection optical system, a reference optical system, a detector, and a counting unit. The light source emits a light. The light superimposition unit is configured to superimpose two lights in a space. The irradiation optical system is configured to irradiate a fluid in a flow passage with one light among a plurality of lights obtained by branching the light from the light source, to form a detection area. The detection optical system is configured to make a scattered light in a direction different from an optical axis of the irradiation optical system, among scattered lights from particles contained in the fluid flowing in the detection area, enter the light superimposition unit. The reference optical system is configured to make another one light among the plurality of lights enter the light superimposition unit as a reference light. The detector is configured to receive an interference light by the scattered light and the reference light at a light receiving element. The interference is obtained by the light superimposition unit. The detector is configured to generate a detection signal corresponding to the interference light. The counting unit is configured to count the particles based on the detection signal generated by the detector. The light superimposition unit is a beam splitter. The light superimposition unit is configured to generate a first interference light and a second interference light. The first interference light is constituted of a transmission component of the scattered light and a reflection component of the reference light. The second interference light is constituted of a reflection component of the scattered light and a transmission component of the reference light. The detector is configured to receive the first interference light and the second interference light at two light receiving elements. The detector is configured to generate the difference between an electrical signal corresponding to the first interference light and an electrical signal corresponding to the second interference light as the detection signal.

Effects of the Invention

With this invention, a particle counter that can count particles with a small particle size at a satisfactory S/N ratio can be obtained.

DESCRIPTION OF EMBODIMENTS

The following describes embodiments of this invention with reference to the drawings.

First Embodiment.

Figure 1:
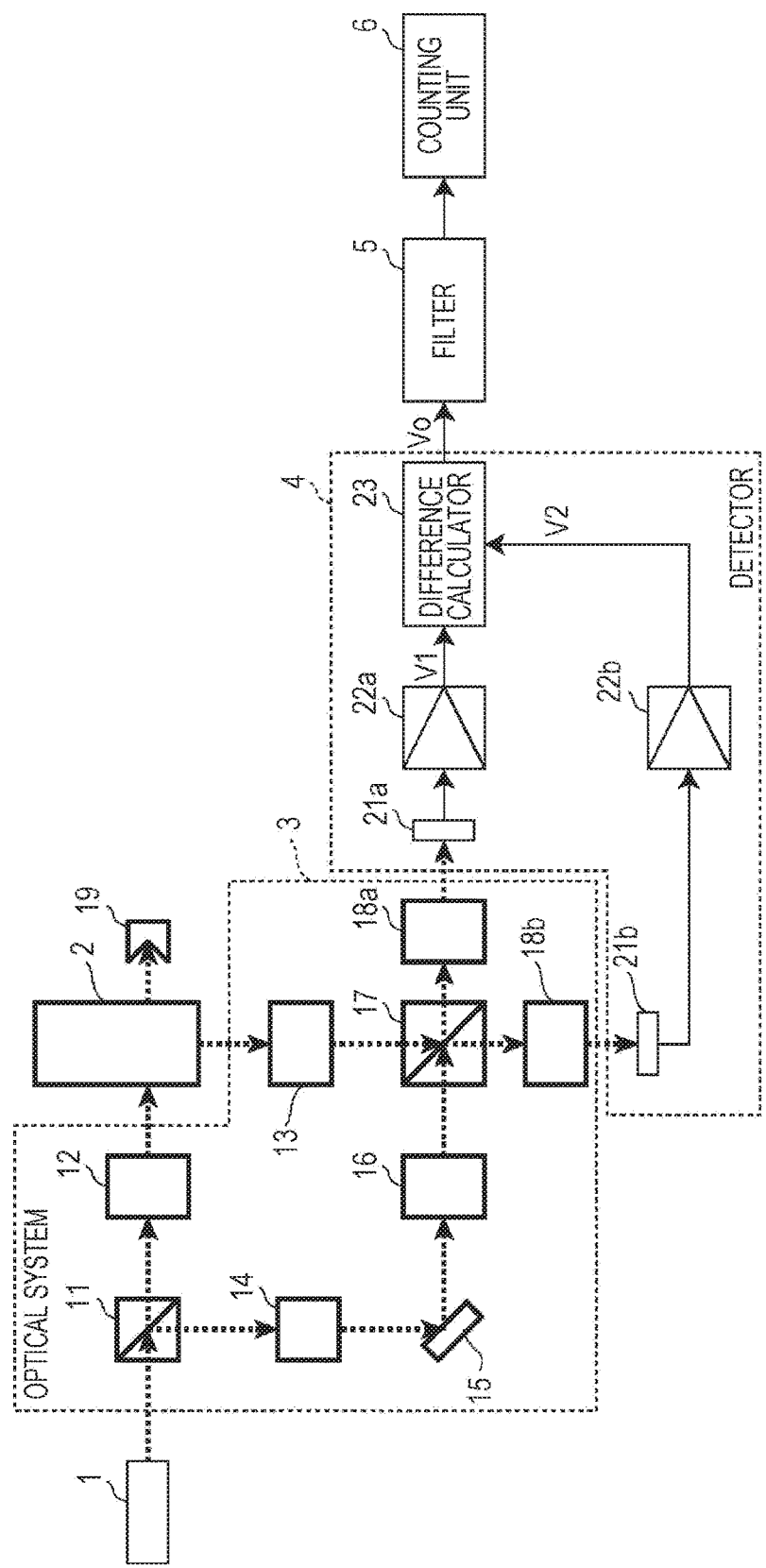
FIG. 1 is a block diagram illustrating a structure of a particle counter according to a first embodiment of this invention.

FIG. 1 is a block diagram illustrating a structure of a particle counter according to the first embodiment of this invention. The particle counter illustrated in FIG. 1 has a light source 1, a flow cell 2, an optical system 3, a detection circuit 4, a filter 5, and a counting unit 6.

The light source 1 is a light source emitting light (laser light here) at a stable frequency. In the embodiment, the light source 1 emits a high-coherence single-mode light. For example, as the light source 1, a laser light source with a wavelength of 532 nm and an output of about 500 mW is used.

The flow cell 2 forms a flow passage for a fluid containing particles to be counted. In the embodiment, the fluid containing particles to be counted is a liquid.

Figure 2:
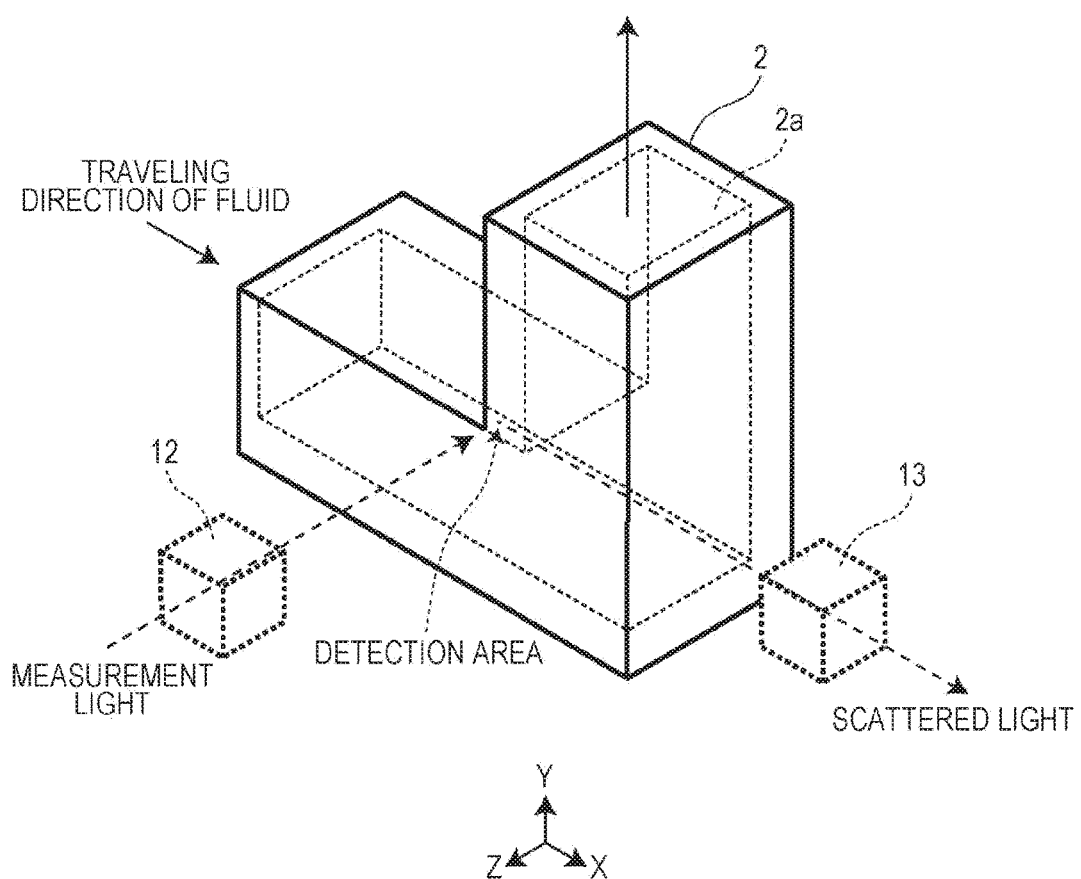
FIG. 2 is a perspective view of an example of a flow cell 2 illustrated in FIG. 1.

FIG. 2 is a perspective view of an example of the flow cell 2 illustrated in FIG. 1. As illustrated in FIG. 2, the flow cell 2 is bent in an L shape. The flow cell 2 is a transparent tubular member that forms a bent flow passage 2a. When the fluid containing particles to be counted is a chemical solution such as isopropyl alcohol, hydrofluoric acid solution, or acetone, the sapphire flow cell 2 is used, for example.

In the flow cell 2, the fluid flowing in the flow passage 2a is irradiated with one light among lights obtained by branching a light from the light source 1, to form a detection area.

The optical system 3 includes a beam splitter 11, an irradiation optical system 12, a detection optical system 13, an attenuator 14, a mirror 15, a beam expander 16, a beam splitter 17, and condensers 18a and 18b.

The beam splitter 11 branches a light from the light source 1 into two lights. One of the lights branched by the beam splitter 11 (hereinafter, called measurement light) enters the irradiation optical system 12. The other light among the lights branched by the beam splitter 11 (hereinafter, called reference light) enters the attenuator 14. For example, the beam splitter 11 branches the light from the light source 1 at a predetermined uneven ratio (for example, 90:10). The intensity of the measurement light is larger than the intensity of the reference light.

The irradiation optical system 12 irradiates the fluid flowing in the flow passage 2a with the measurement light from a direction (in this example, the vertical direction, namely, a Z direction in FIG. 2) different from a travelling direction of the fluid in the flow passage 2a of the flow cell 2 (an X direction in FIG. 2). The irradiation optical system 12 uses a lens group as described in JP-A-2003-270120, for example, to shape the laser beam in such a manner as to enhance its energy density.

The detection optical system 13 makes the scattered light from the particles in the flow passage 2a by the foregoing irradiation of the measurement light enter a predetermined incident surface of the beam splitter 17. For example, the detection optical system 13 uses a condensing lens or an optical system including a pin hole for blocking background light and condensing lenses arranged on the front and rear stages of the pin hole.

In the embodiment, the measurement light enters the flow passage 2a from a direction different from the optical axis of the detection optical system 13. Accordingly, the detection optical system 13 makes the scattered light of side scattering enter the beam splitter 17.

Figure 3:
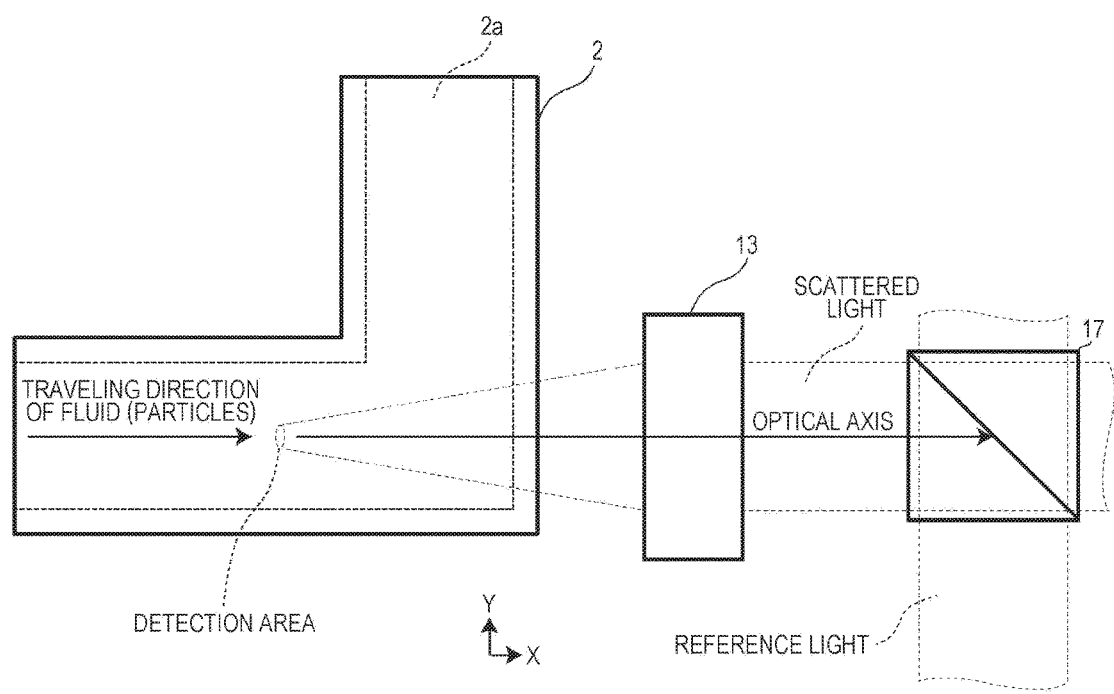
FIG. 3 is a drawing for describing the arrangement of the flow cell 2, a detection optical system 13, and a beam splitter 17 illustrated in FIG. 1.

FIG. 3 is a drawing for describing the arrangement of the flow cell 2, the detection optical system 13, and the beam splitter 17 illustrated in FIG. 1. Specifically, as illustrated in FIG. 3, the detection optical system 13 makes a scattered light emitted along the travelling direction of the fluid (namely, the particles) in the detection area enter the beam splitter 17 among scattered lights emitted from the particles and the fluid in the flow passage 2a.

In the embodiment, as illustrated in FIG. 3, the travelling direction (X direction) of the fluid (namely, the particles) is identical to the direction of the optical axis of the detection optical system 13. The scattered light within a predetermined solid angle from the center of the detection area enters the beam splitter 17.

Thus, among the scattered lights emitted from the particles in the flow passage 2a, the side scattered light emitted along the travelling direction (X direction) of the fluid in the detection area is detected. Accordingly, a change in a light path length, a distance between the particles and the beam splitter 17, in association with the movement of the particles in the detection area becomes larger than the case of the detection of the scattered lights from the particles in another direction (a direction other than the X direction). This point will be described later.

Meanwhile, the reference light branched by the beam splitter 11 enters the attenuator 14.

The attenuator 14 attenuates the intensity of the light at a predetermined ratio. As the attenuator 14, a neutral density (ND) filter is used, for example. The mirror 15 reflects the reference light emitted from the attenuator 14 and makes the reference light enter the beam expander 16. For example, the beam splitter 11 and the attenuator 14 configure the intensity of the reference light to be approximately one ten thousandth of the intensity of the light emitted from the light source 1. The intensity of the reference light that enters the beam splitter 17 is set according to the particle size of the particles to be counted, the intensity of the scattered light, and the like. The attenuation rate of the attenuator 14 and the like are set to achieve the intensity of the reference light.

The beam expander 16 enlarges a beam diameter of the reference light to a predetermined diameter. The beam expander 16 employs the reference light with the enlarged beam diameter as an approximate parallel light and makes the approximate parallel light enter a predetermined incident surface (an incident surface different from the incident surface of the scattered light) of the beam splitter 17.

In the embodiment, the detection optical system 13, the mirror 15, and the beam expander 16 are configured such that the wave front shape of scattered light and the wave front shape of reference light approximately match with each other at the beam splitter 17. In the embodiment, the detection optical system 13 and the beam expander 16 emit the scattered light and the reference light respectively as approximately parallel lights. The wave front shapes of the scattered light and the reference light may be curved surfaces.

In addition, the detection optical system 13, the mirror 15, and the beam expander 16 are configured such that their polarizing angles at the beam splitter 17 match with one another.

Thus, in the embodiment, to further enhance the degree of interference, the attenuator 14, the mirror 15, the beam expander 16, and others, being installed in the light path of the reference light, control the intensity, a polarizing angle, and a wave front shape of the reference light.

The beam splitter 17 superimposes the incident scattered light on the incident reference light in the space so that they interfere with each other to mutually strengthen or weaken. In this embodiment, the beam splitter 17 is provided separately from the beam splitter 11. At the beam splitter 17, a phase difference between the scattered light and the reference light changes depending on changes in the light path length resulting from the movement of the particles in the detection area. In addition, the intensity of the interference light changes depending on the light passing through or reflected on the beam splitter 17 itself. As described above, the side scattered light emitted along the travelling direction of the fluid in the detection area is detected. This largely and quickly changes the light path length of the scattered light resulting from the movement of the particles in the detection area. Accordingly, the velocity at which the intensity of the interference light changes becomes high. Therefore, the intensity of the interference light changes depending on a cycle (namely, on a frequency) according to the velocity in the travelling direction of the fluid (namely, the particles) in the detection area. For the period during which no scattered light by the particle enters, the lights (the transmission component and the reflection component) obtained by branching of the scattered light due to the fluid and the reference light interfere with each other and are emitted from the beam splitter 17. The changes in the interference light in this case are smaller than changes in the interference light due to the particles.

The condenser 18a condenses light emitted from one emission surface of the beam splitter 17 and makes the light enter a light receiving element 21a. The condenser 18b condenses the light emitted from another emission surface of the beam splitter 17 and makes the light enter the light receiving element 21b. As the condensers 18a and 18b, condensing lenses are used, for example.

Figure 4:
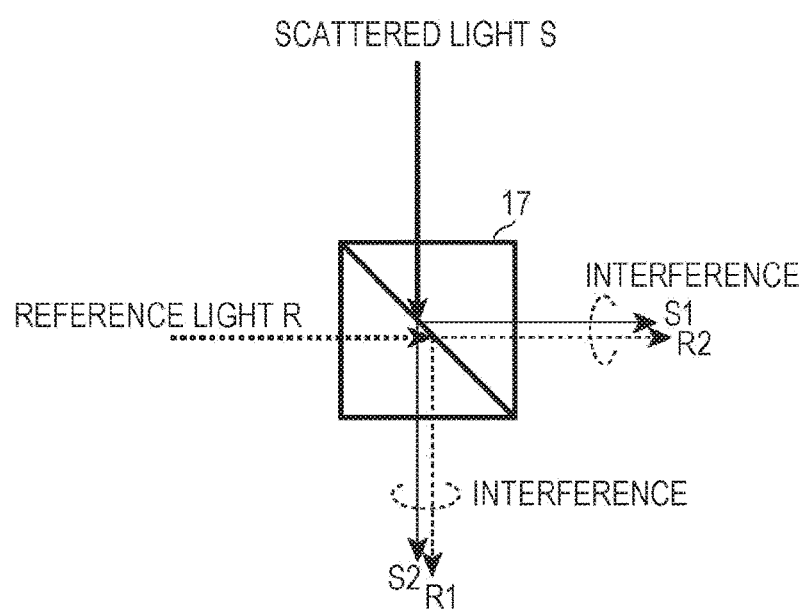
FIG. 4 is a drawing for describing a branch of light at the beam splitter 17 illustrated in FIG. 1.

FIG. 4 is a drawing describing the branch of light at the beam splitter 17 illustrated in FIG. 1. As illustrated in FIG. 4, scattered light S and reference light R enter the beam splitter 17 such that the optical axis of a reflection component Si of the scattered light S and the optical axis of a transmission component R2 of the reference light R match with each other and further the optical axis of a transmission component S2 of the scattered light S and the optical axis of a reflection component R1 of the reference light R match with each other. Therefore, the beam splitter 17 emits a first interference light generated by the reflection component Si of the scattered light S and the transmission component R2 of the reference light R and a second interference light generated by the transmission component S2 of the scattered light S and the reflection component R1 of the reference light R. The first interference light and the second interference light enter light receiving elements 21a and 21b of the detector 4 via the condensers 18a and 18b, respectively.

The scattered light S and the reference light R each enters the light branch surface of the beam splitter 17 at an angle of approximately 45 degrees. The transmission components S2 and R2 are in phases as those of the scattered light S and the reference light R, respectively. The phases of the reflection components S1 and R1 lag by 90 degrees relative to the scattered light S and the reference light R, respectively. Therefore, the first interference light and the second interference light become opposite phases to one another.

In addition, preferably, the ratio of the transmission component to the reflection component in the beam splitter 17 is 50:50. However, the ratio may be uneven such as 60:40. When the ratio of the transmission component to the reflection component in the beam splitter 17 is uneven, the gains of amplifiers 22a and 22b are set according to the ratio such that the transmission component of the reference light in an electrical signal V1 and the reflection component of the reference light in an electrical signal V2 become equal.

A beam damper 19 absorbs the light having passed through the flow cell 2. This ensures restraining the influence on the optical system 3 caused by irregular light reflection, leakage, and others of the light having passed through the flow cell 2.

The detector 4 receives the interference light obtained by the beam splitter 17 at the respective light receiving elements 21a and 21b. The detector 4 generates a detection signal Vo corresponding to the difference between the interference light. In the embodiment, as illustrated in FIG. 1, the detector 4 includes the light receiving elements 21a and 21b, the amplifiers 22a and 22b, and a difference calculator 23.

The light receiving elements 21a and 21b are photodetectors such as a photodiode and a phototransistor and each outputs the electrical signals corresponding to the incident lights. The amplifiers 22a and 22b amplify the electrical signals outputted from the light receiving elements 21a and 21b by predetermined gains. The difference calculator 23 calculates the difference between the electrical signal V1, which is obtained by the light receiving element 21a and corresponds to the first interference light, and the electrical signal V2, which is obtained by the light receiving element 22a and corresponds to the second interference light, and outputs this difference as the detection signal Vo.

In a state where a scattered light component due to the particles is not contained (the scattered light component due to the fluid and a reference light component), the gains of the amplifiers 22a and 22b are adjusted such that a voltage of the electrical signal V1 becomes identical to a voltage of the electrical signal V2. Instead, one of the amplifiers 22a and 22b may be disposed and the gain of the amplifier may be adjusted so as to match both of the foregoing voltages. In the case where the voltage of the electrical signal of the light receiving element 21a is identical to the voltage of the electrical signal of the light receiving element 22a, the amplifiers 22a and 22b may be omitted.

Figure 5:
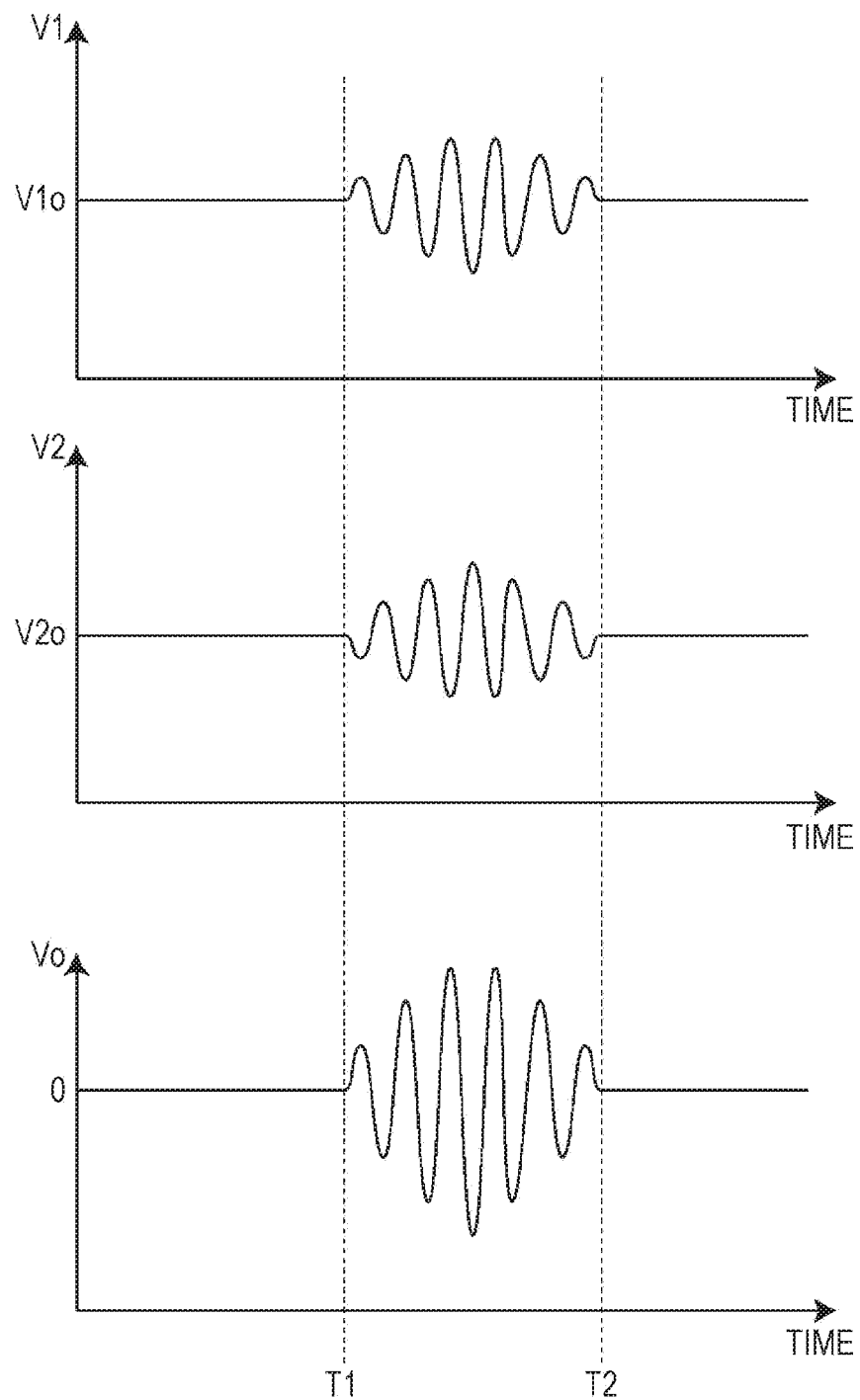
FIG. 5 is a timing chart for describing a detection signal obtained by a detector 4 illustrated in FIG. 1.

FIG. 5 is a timing chart describing the detection signal obtained by the detector 4 illustrated FIG. 1.

When a certain particle passes through the detection area during a period of a time T1 to a time T2, a scattered light is generated due to the particles in that period. Then, as the particle moves in the travelling direction (X direction) in the detection area, the light path length from the particle to the light branch surface of the beam splitter 17 changes. Accordingly, the phase difference between the scattered light due to the particles and the reference light changes. The intensity of the interference light (amplitude) changes to strengthen or weaken mutually.

Therefore, as illustrated in FIG. 5, in the period during which the particles pass through the detection area, the electrical signal V1 changes positively or negatively relative to a reference of a voltage V1o without the particles depending on the degree of interference. Except for the period, the electrical signal V1 has the voltage V1o. Similarly, in the period, the electrical signal V2 changes positively or negatively relative to a reference of a voltage V2o without the particles depending on the degree of interference. Except for the period, the electrical signal V2 has the voltage V2o. However, the AC components of the electrical signals V1 and V2 in that period are opposite in phase to one another.

The reference voltages V1o and V2o of the electrical signals V1 and V2 outputted from the amplifiers 22a and 22b are equal to one another. Accordingly, as illustrated in FIG. 5, the detection signal Vo obtained by the difference calculator 23 has an AC component with a larger amplitude (about double) than the AC component resulting from the interferences of the respective electrical signals V1 and V2 in the period during which the particles pass through the detection area. The detection signal Vo has a voltage of almost zero except for the period.

In the embodiment of this invention, the scattered light emitted along the travelling direction (X direction) of the fluid in the detection area is detected. Accordingly, when the particles pass through the detection area, a change in an amount of light path becomes larger. When the particles pass through in the period of the time T1 to the time T2, the movement distance of the particles becomes the change in light path length between the particles and the light branch surface of the beam splitter 17. Accordingly, the number of changes in interference increases as compared to the case in which the scattered light due to the particles is detected in other directions (other than the X direction) (that is, phase rotations of the interference light increases). This means that the number of waves in the electrical signals outputted from the light receiving elements 21a and 21b increases in the period of the time T1 to the time T2. This makes it easier to detect the signals; therefore, the S/N ratio is improved. However, there is no limitation in the detection direction of the scattered light as long as the scattered light can be detected.

The scattered light (background light) from the liquid as a fluid medium is generated in the entire detection area. Further, background lights from different positions are also present. However, the background lights are canceled out by the difference calculation. Accordingly, the AC component of the detection signal Vo resulting from the interference of the background light is smaller than the AC component resulting from the interference of the scattered light due to the particles.

In the embodiment, the particle size of the particles to be counted is smaller than the wavelength of the light emitted from the light source 1. Accordingly, the intensity of the scattered light caused by Rayleigh scattering is proportional to the sixth power of the particle size. In contrast, the intensity of the interference light generated by the scattered light and the reference light is proportional to the third power of the particle size. Accordingly, compared with the direct detection of the scattered light, the detection of the interference light decreases the reduction in the intensity of light with the case of the small particle size.

The difference between the maximum value and the minimum value of the intensity of the interference light by the scattered light and the reference light (the difference in the interference light intensity between when the phase difference between the scattered light and the reference lights is zero and when this phase difference is 180 degrees) is proportional to the product of an electric field intensity Er of the reference light and an electric field intensity Es of the scattered light. Accordingly, enhancing the intensity of the reference light obtains an interference light of sufficiently strong. As the result, a detection signal with a sufficiently large amplitude is obtained. The larger the intensity of the reference light, the larger the intensity of the interference light is. The intensity of the reference light is set to a value at which the detection signal is properly processable according to dynamic ranges of the detector 4, the filter 5, and the counting unit 6.

For example, with a scattered light intensity Is of particles with the particle size of 20 nm of $7.0 \times 10^{-6}$ µW, the electric field intensity Es of the scattered light becomes $5.8 \times 10^{-3}$ V/m. Meanwhile, with a reference light intensity Ir of 1.2 µW, the electric field intensity Er of the reference light becomes 2.4 V/m. Then, the interference of the scattered light with the reference light on the entire wave front region configures the foregoing difference in interference light intensity to $1.2 \times 10^{-2}$ µW, approximately 1600 times of the scattered light intensity, being amplified to a level equivalent to the scattered light intensity from the particles with the particle size of 70 nm.

The filter 5 performs a filtering process on the detection signal Vo generated by the detector 4. The filter 5 lets pass the frequency component (that is, the frequency component of the interference light) corresponding to the fluid velocity (that is, the moving velocity of the particles) in the flow passage 2a, and performs the filtering process that attenuates the frequency components other than the frequency component corresponding to the travelling velocity of the fluid on the detection signal Vo. Accordingly, the noise component of the detection signal Vo is attenuated. Therefore, the S/N ratio of the detection signal Vo is improved. The passband frequency is determined in advance by the moving velocity of the particles, the wavelength of the measurement light (that is, the wavelength of the light source 1), and the like. The filter 5 uses a band-pass filter. The filter 5 may use a low-pass filter when the frequency of the noise is higher than the frequency of the interference light. The filter 5 may use a high-pass filter when the frequency of the noise is lower than the frequency of the interference light.

The counting unit 6 counts the particles based on the detection signal Vo. In the embodiment, the counting unit 6 counts the particles based on the detection signal Vo after the filtering process by the filter 5. For example, when the counting unit 6 detects the AC components continuous during the foregoing period (that is, the frequency components of the interference light) in the detection signal Vo, the counting unit 6 compares the amplitudes to predetermined thresholds decided by the particle size. The counting unit 6 counts one particle by a particle size that differentiates between particles.

Next, operations of the particle counter according to the first embodiment will be explained.

The light source 1 emits the laser light. The beam splitter 11 branches the laser light into the measurement light and the reference light. After being attenuated by the attenuator 14, the reference light goes through the mirror 15 and the beam expander 16 and then is entered into the beam splitter 17 as the approximately parallel light.

Meanwhile, the irradiation optical system 12 makes the measurement light enter the detection area in the flow cell 2. When a particle passes through the detection area, a scattered light is generated due to the particle during the period of the particle passing through the detection area. The detection optical system 13 makes scattered light emitted along the travelling direction (X direction) of the fluid in the flow passage 2a of the flow cell 2 enter the beam splitter 17 as approximately parallel light.

Thus, in the period during which the particles pass through the detection area, the reference light and the scattered light from the particles and the reference light enter the beam splitter 17. The beam splitter 17 emits the interference lights resulting from the interference between the scattered light and the reference light.

In the period during which the particles pass through the detection area, the beam splitter 17 emits the interference lights, and the interference lights are received by the respective light receiving elements 21a and 21b. The detector 4 outputs the electrical signal corresponding to the intensities of the interference lights as the detection signal Vo. In particular, in the first embodiment, the detection signal Vo is generated based on the difference between the foregoing first interference light and the foregoing second interference light being opposite in phases to each other. Accordingly, the detection signal Vo of the AC components having an amplitude about two times of the electrical signals V1 and V2 are obtained.

The filter 5 performs the foregoing filtering process on the detection signal. The counting unit 6 counts the particles based on the detection signal after the filtering process.

As described above, according to the embodiment, the irradiation optical system 12 irradiates the fluid in the flow passage 2a, from the direction different from the flowing direction of the fluid, with one light among the plurality of lights obtained by branching the light from the light source 1, to form the detection area. The detection optical system 13 makes the scattered light with a different direction from the optical axis of the irradiation optical system 12 enter the beam splitter 17 among the scattered lights from the particles contained in the fluid in the detection area. Meanwhile, the beam expander 16 makes another light among the plurality of lights enter the beam splitter 17 as the reference light. The detector 4 receives the interference light, due to the scattered light and the reference light, obtained by the beam splitter 17 by the light receiving elements and generates the detection signal corresponding to the interference light. The counting unit 6 counts the particles based on this detection signal.

Accordingly, the passage of the particles is detected based on the interference lights resulting from the passage of particles in the detection area. Therefore, it is possible to count small-diameter particles in the fluid with a satisfactory S/N ratio as compared to the case of detecting the scattered light.

Second Embodiment

In the first embodiment, the first interference light and the second interference light are received as interference lights by the scattered light from the particles and the reference light. The difference between the electrical signals V1 and V2 of both is used as the detection signal Vo. In the second embodiment, instead of this, the electrical signal from either the first interference light or the second interference light is used as the detection signal Vo. In this case, the detection signal Vo also contains an AC component resulting from the interference light by the scattered light from the particles and the reference light. Accordingly, the particles can be counted in the same manner. In this case, one light receiving element may be provided.

Other components of a particle counter according to the second embodiment are the same as those of the first embodiment, and descriptions thereof will be omitted.

The foregoing respective embodiments are preferred examples of this invention. However, this invention is not limited to the foregoing ones. This invention can be modified and changed in various manners without deviating from the gist of this invention.

For example, the foregoing first and second embodiments include the beam expander 16 at the optical path for the reference light. Instead or additionally, a beam expander may be disposed at a preceding stage of the beam splitter 11. In the first and second embodiments, the one mirror 15 is used as illustrated in FIG. 1. Instead, three mirrors may be used to adjust three-dimensionally the direction of the light path. In addition, in the first and second embodiments, the scattered light from the particles and the reference light are superimposed by the use of the beam splitter 17. Instead, a polarization prism may be used.

In the first and second embodiments, the filter 5 may be omitted when the noise component of the detection signal Vo is small. In that case, the detection signal Vo is inputted directly into the counting unit 6.

In the first and second embodiments, the light source 1 is a light source that emits a single-mode and high-coherence laser beam. Instead, a light source emitting a multi-mode and relatively low-coherence laser beam may be used. However, it is preferable to use the light source having an energy distribution in which the scattered light from the particles interferes with the reference light at any position in the detection area.

In the first and second embodiments, the filter 5 and the counting unit 6 may be analog circuits or digital circuits. When the filter 5 and the counting unit 6 are digital circuits, the detection signal Vo is subjected to analog-digital conversion at the preceding stage of the filter 5.

In the first and second embodiments, as illustrated in FIG. 1, a so-called Mach-Zehnder interference optical system in which the branching of light and the superimposition of light are performed by the different beam splitters 11 and 17 is employed. Instead, a Michelson or any other type interference optical system may be used.

In addition, the particle counters according to the first and second embodiments are liquid-borne particle counters. The particle counters according to the first and second embodiments may be applied to airborne particle counters.

INDUSTRIAL APPLICABILITY

This invention is applicable to particle counters for chemical solutions, for example.

DESCRIPTION OF REFERENCE SIGNS

1: Light source
4: Detector
5: Filter
6: Counting unit
11: Beam splitter (one example of light branching unit)
12: Irradiation optical system
13: Detection optical system
16: Beam expander (one example of reference optical system)
17: Beam splitter (one example of light superimposition unit)
21a, 21b: Light receiving element

The invention claimed is:

1. A particle counter comprising:
a light source that emits light;
a light superimposition unit configured to superimpose two lights in a space;
an irradiation optical system configured to irradiate, from a direction different from a travelling direction of a fluid flowing in a flow passage, the fluid with one light among a plurality of lights obtained by branching the light from the light source to form a detection area;
a detection optical system configured to make a scattered light in a direction different from an optical axis of the irradiation optical system, among scattered lights from particles contained in the fluid in the detection area, enter the light superimposition unit;
a reference optical system configured to make another one light among the plurality of lights enter the light superimposition unit as a reference light;
a detector configured to receive an interference light by the scattered light and the reference light at a light receiving element, the interference light being obtained by the light superimposition unit, the detector being configured to generate a detection signal corresponding to the interference light; and a counting unit configured to count the particles based on the detection signal, wherein:

the light superimposition unit is a beam splitter, the light superimposition unit being configured to generate first interference light and second interference light, the first interference light being constituted of a transmission component of the scattered light and a reflection component of the reference light, the second interference light being constituted of a reflection component of the scattered light and a transmission component of the reference light, and the detector is configured to receive the first interference light and the second interference light at two light receiving elements, the detector being configured to generate the difference between an electrical signal corresponding to the first interference light and an electrical signal corresponding to the second interference light as the detection signal.

2. The particle counter according to claim 1, wherein:
the detection optical system makes, among the scattered lights emitted from the particles in the flow passage, scattered light emitted along the travelling direction of the fluid in the detection area enter the light superimposition unit.

3. The particle counter according to claim 2, further comprising;
a filter configured to perform a filtering process on the detection signal generated by the detector,
wherein the filter performs the filtering process on the detection signal, the filtering process being configured to make a frequency component corresponding to a progress velocity of the fluid pass through, the filtering process being configured to attenuate a frequency component other than the frequency component corresponding to the progress velocity of the fluid, and
the counting unit is configured to count the particles based on the detection signal after the filtering process by the filter.

4. The particle counter according to claim 3, wherein:
the detection optical system and the reference optical system are configured to emit the scattered light and the reference light such that a wave front shape of the scattered light approximately matches a wave front shape of the reference light.

5. The particle counter according to claim 4, comprising:
a light branching unit disposed separately from the light superimposition unit, the light branching unit being configured to branch the light from the light source into the plurality of lights.

6. The particle counter according to claim 3, comprising:
a light branching unit disposed separately from the light superimposition unit, the light branching unit being configured to branch the light from the light source into the plurality of lights.

7. The particle counter according to claim 2, wherein:
the detection optical system and the reference optical system are configured to emit the scattered light and the reference light such that a wave front shape of the scattered light approximately matches a wave front shape of the reference light.

8. The particle counter according to claim 7, comprising:
a light branching unit disposed separately from the light superimposition unit, the light branching unit being configured to branch the light from the light source into the plurality of lights.

9. The particle counter according to claim 2, comprising:
a light branching unit disposed separately from the light superimposition unit, the light branching unit being configured to branch the light from the light source into the plurality of lights.

10. The particle counter according to claim 1, further comprising;
a filter configured to perform a filtering process on the detection signal generated by the detector,
wherein the filter performs the filtering process on the detection signal, the filtering process being configured to make a frequency component corresponding to a progress velocity of the fluid pass through, the filtering process being configured to attenuate a frequency component other than the frequency component corresponding to the progress velocity of the fluid, and
the counting unit is configured to count the particles based on the detection signal after the filtering process by the filter.

11. The particle counter according to claim 10, wherein:
the detection optical system and the reference optical system are configured to emit the scattered light and the reference light such that a wave front shape of the scattered light approximately matches a wave front shape of the reference light.

12. The particle counter according to claim 11, comprising:
a light branching unit disposed separately from the light superimposition unit, the light branching unit being configured to branch the light from the light source into the plurality of lights.

13. The particle counter according to claim 10, comprising:
a light branching unit disposed separately from the light superimposition unit, the light branching unit being configured to branch the light from the light source into the plurality of lights.

14. The particle counter according to claim 1, wherein:
the detection optical system and the reference optical system are configured to emit the scattered light and the reference light such that a wave front shape of the scattered light approximately matches a wave front shape of the reference light.

15. The particle counter according to claim 14, comprising:
a light branching unit disposed separately from the light superimposition unit, the light branching unit being configured to branch the light from the light source into the plurality of lights.

16. The particle counter according to claim 1, comprising:
a light branching unit disposed separately from the light superimposition unit, the light branching unit being configured to branch the light from the light source into the plurality of lights.

* * * * *